(12) United States Patent
Ahern et al.

(10) Patent No.: US 7,803,305 B2
(45) Date of Patent: Sep. 28, 2010

(54) PROCESS FOR FORMING MULTILAYER CONTAINERS

(75) Inventors: Brian F. Ahern, San Francisco, CA (US); Nicholas A. Grippi, Wayne, NJ (US); Paul R. Soskey, Neshanic Station, NJ (US); Donald J. Carano, Pequannock, NJ (US); Norman J. Hutton, Franklin Lakes, NJ (US); Danielle M. DeSalvo, Lake Hiawatha, NJ (US); Gregory L. Lusardi, Hackettstown, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1240 days.

(21) Appl. No.: 10/480,540

(22) PCT Filed: Jun. 14, 2002

(86) PCT No.: PCT/US02/18972
§ 371 (c)(1),
(2), (4) Date: Jul. 2, 2004

(87) PCT Pub. No.: WO02/102571
PCT Pub. Date: Dec. 27, 2002

(65) Prior Publication Data
US 2005/0037165 A1    Feb. 17, 2005

(51) Int. Cl.
*B29C 45/16* (2006.01)
*B29C 45/13* (2006.01)
*B29C 45/72* (2006.01)

(52) U.S. Cl. ............... 264/328.8; 264/255; 264/328.9; 264/328.14; 264/328.15; 264/328.16

(58) Field of Classification Search ................. None
See application file for complete search history.

(56) References Cited

U.S. PATENT DOCUMENTS 3,797,984 A * 3/1974 Yago et al. ................ 425/543

(Continued)

FOREIGN PATENT DOCUMENTS

EP    0512612    11/1992

(Continued)

OTHER PUBLICATIONS

Gabriele M C: "Coninjection Boosts Barrier Properties of Pet Bottles" Modern Plastics International, McGraw-Hill, Inc. Lausanne, CH, vol. 27, No. 9, Sep. 1, 1997, pp. 106-107, 109,11,XP000699139 ISSN:0026-8283.

(Continued)

*Primary Examiner*—Edmund H. Lee
(74) *Attorney, Agent, or Firm*—Mark Lindsey

(57) ABSTRACT

A co-injection process is provided for fabricating improved multi-layer containers, including but not limited to blood collection tubes, evacuated blood collection tubes, culture bottles, centrifuges tubes, and syringe barrels. The container includes a tube (10) having a bottom wall (12) and a side wall (14) with an open end (18). The container can be provided with a stopper having an upper portion (22) and a skirt with an outside portion (30), a well (34) and a cavity (36). The tube and stopper assembly can be used for medical purposes including containing a blood sample within an enclosed interior space (40).

20 Claims, 9 Drawing Sheets

U.S. PATENT DOCUMENTS

| | | | |
|---|---|---|---|
| 4,497,621 A | * 2/1985 | Kudert et al. | 425/145 |
| 4,525,134 A | * 6/1985 | McHenry et al. | 425/130 |
| 4,715,802 A | * 12/1987 | Arai | 425/130 |
| 4,965,028 A | * 10/1990 | Maus et al. | 264/297.2 |
| 5,162,122 A | * 11/1992 | Loren | 425/130 |
| 5,306,270 A | 4/1994 | MaCartney | |

FOREIGN PATENT DOCUMENTS

| | | | |
|---|---|---|---|
| JP | 55139228 | | 10/1980 |
| JP | 57-115332 | * | 7/1982 |
| JP | 61230911 | | 10/1986 |
| JP | 03153328 | | 7/1991 |
| JP | 9-141689 | * | 6/1997 |
| JP | 10298358 | | 11/1998 |

OTHER PUBLICATIONS

Patent Abstracts of Japan vol. 0050, No. 06, Jan. 16, 1981-& JP 55 139228 A (Toppan Printing Co Ltd), Oct. 30, 1980-& Database WPI Section Ch, Week 198050 Derwent Publications Ltd., London, GB; AN 1980-89139C XP002269549 & JP 55 139228 A (Toppan Printing Co Ltd), Oct. 30, 1980.

Database WPI Section Ch, Week 199904 Derwent Publications Ltd., London, GB; AN 1999-040831 XP002269550 & JP 10 298358 A (Mitsui Petrochem Ind Co Ltd), Nov. 10, 1998.

Patent Abstracts of Japan vol. 0110, No. 76, Mar. 7, 1987-& JP 61 230911 A (Toyo Seikan Kaisha Ltd), Oct. 15, 1986.

Patent Abstracts of Japan vol. 0153, No. 81, Sep. 26, 1991-& JP 03 153328 A (Dainippon Printing Co Ltd), Jul. 1, 1991.

* cited by examiner

US 7,803,305 B2

PROCESS FOR FORMING MULTILAYER CONTAINERS

BACKGROUND OF THE INVENTION

1. Field of the Invention

This invention relates to plastic articles and more particularly relates to medical articles having improved gas and liquid vapor barriers.

2. Description of the Related Art

Polypropylene (PP) has long been used in molding and extruding operations for articles such as plastic medical containers and films for the food packaging industry. Polyethylene terephthalate (PET) has more recently been used in molding and extruding operations for these articles. However, PP and PET are somewhat permeable to nitrogen, oxygen, and other gases and vapors. As a result, PP and PET containers are inherently subject to transmission of gases. As the medical industry begins to place increased emphasis on the use of plastic medical products, these permeability problems have become more acute.

In particular, evacuated blood collection tubes must meet certain performance standards. Such performance standards generally include the ability to maintain greater than about 90% original draw volume over a one year period, and gas permeability clearly is detrimental to this need. Moreover, materials must also be capable of being sterilized by radiation, and substantially avoid interfering with tests and analysis. Thus, materials for such containers not only must resist gas and liquid vapor permeability problems, but they must also meet several other requirements.

Various techniques have therefore been devised in an attempt to reduce gas and vapor permeability of containers fabricated from PP, PET and other resins. Such techniques include addition of inorganic fillers, coating the containers with resins having barrier properties, plasma chemical vapor deposition coating of inorganic materials, and blending, laminating or co-extruding the resins with barrier resins.

While such efforts have offered some improvement, the need to consistently meet high performance standards demands further improvement.

SUMMARY OF THE INVENTION

The invention address the problems of the prior art, and provides a process for fabricating improved containers meeting the needs discussed above. Such containers include but are not limited to blood collection tubes, evacuated blood collection tubes, centrifuge tubes, culture bottles, and syringe barrels.

In one embodiment, the process of the invention involves providing a first molten polymeric material and a second molten polymeric material, the first and second polymeric materials being non-compatible, and directing the first and second molten polymeric materials through a nozzle section into a mold cavity that comprises a region for integrally forming the bottom wall of the container. The first and second molten polymeric materials co-flow in the mold cavity for at least a portion of the fabrication process. During the co-flow, the nozzle section directs the first and second molten polymeric materials into the mold cavity as inner and outer skin layers of the first molten polymeric material with an core layer of the second molten polymeric material between the inner and outer skin layers.

In another embodiment, a tube of the invention comprises a bottom wall, a top edge, and a sidewall between the bottom wall and the top edge. At least the sidewall comprises inner and outer polymeric skin layers with a polymeric core layer located between and directly adjacent the inner and outer polymeric skin layers, with the polymeric skin layers being non-compatible with the polymeric core layer. A tube having non-compatible polymers, yet without the need for adhesive or tie layers between the distinct polymers is thereby achieved.

DETAILED DESCRIPTION

Containers according to the invention include, for example, tubes, bottles, vials, flasks, syringes, and single use disposable containers. Particularly useful tubes are those for blood collection. The invention is described below with respect to an evacuated blood collection tube, but it will be apparent to one skilled in the art that the description is equally applicable to any other container.

All containers, regardless of the intended end use, must meet performance standards to be acceptable for use. Evacuated plastic blood collection tubes must generally maintain a particular draw volume over an anticipated shelf life. This requires a barrier to inhibit passage of atmospheric gases through the polymer wall, which would reduce the draw volume. Liquid vapor permeation through the tube wall must be similarly inhibited to reduce deterioration of dry blood analysis additives, or maintain critical liquid additives, frequently introduced into the tube at the time of manufacture.

Figure 1:
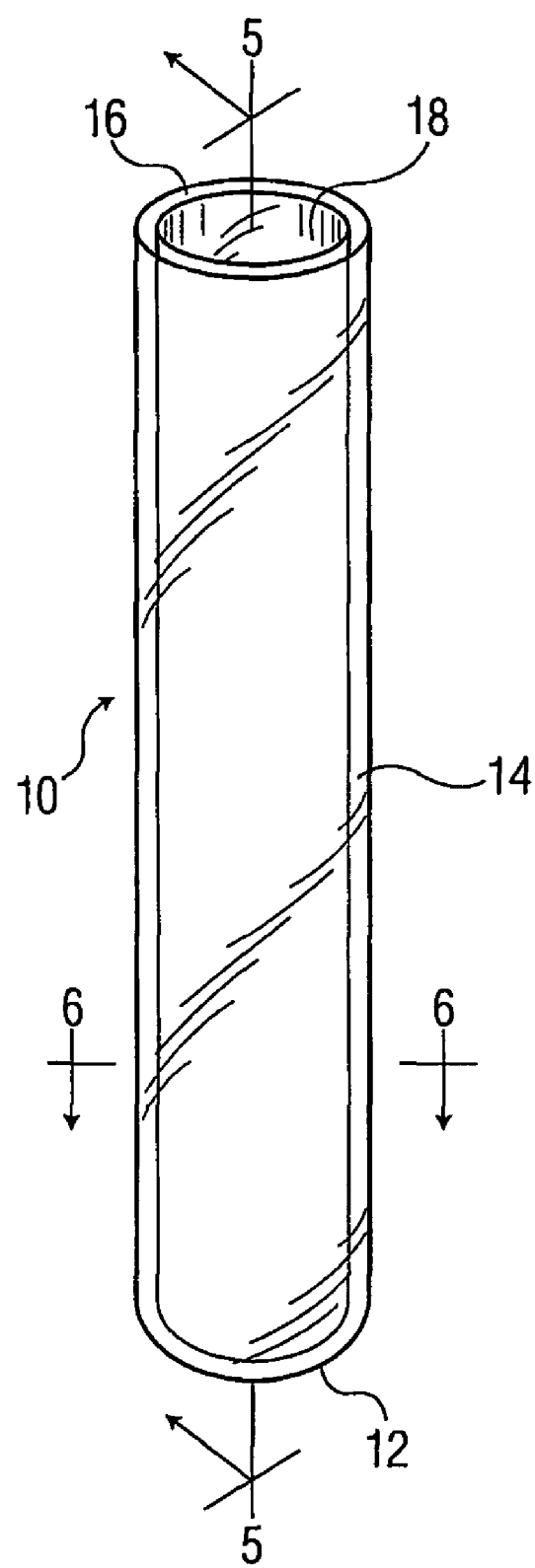
FIG. 1 is a perspective view of a collection tube with the multi-layer wall of the invention.
Figure 2:
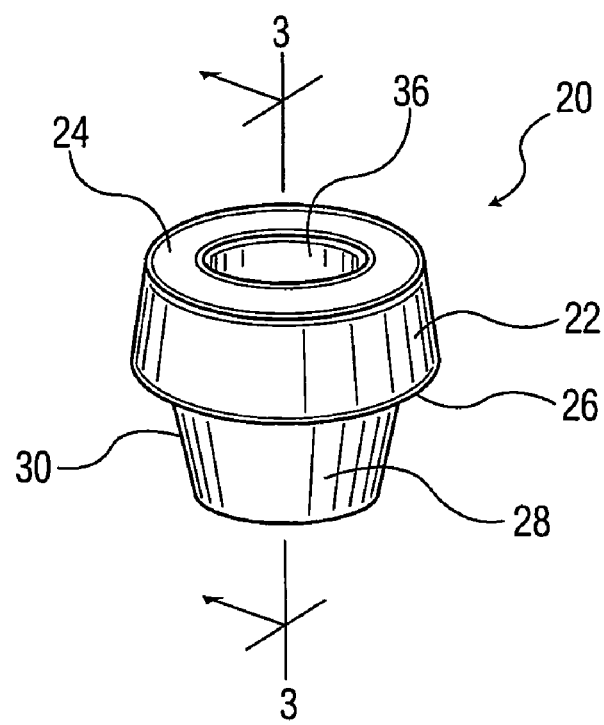
FIGS. 2 and 3 illustrate a puncturable closure for the tube of FIG. 1, with FIG. 3 showing the cross-section at line 3-3.
Figure 3:
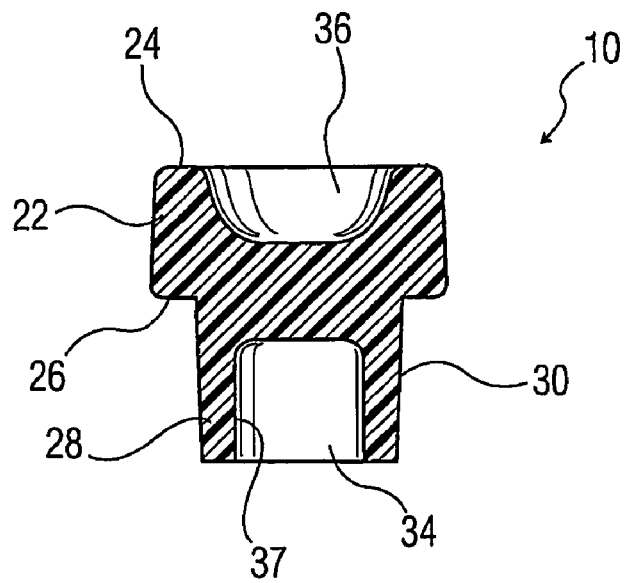
Figure 4:
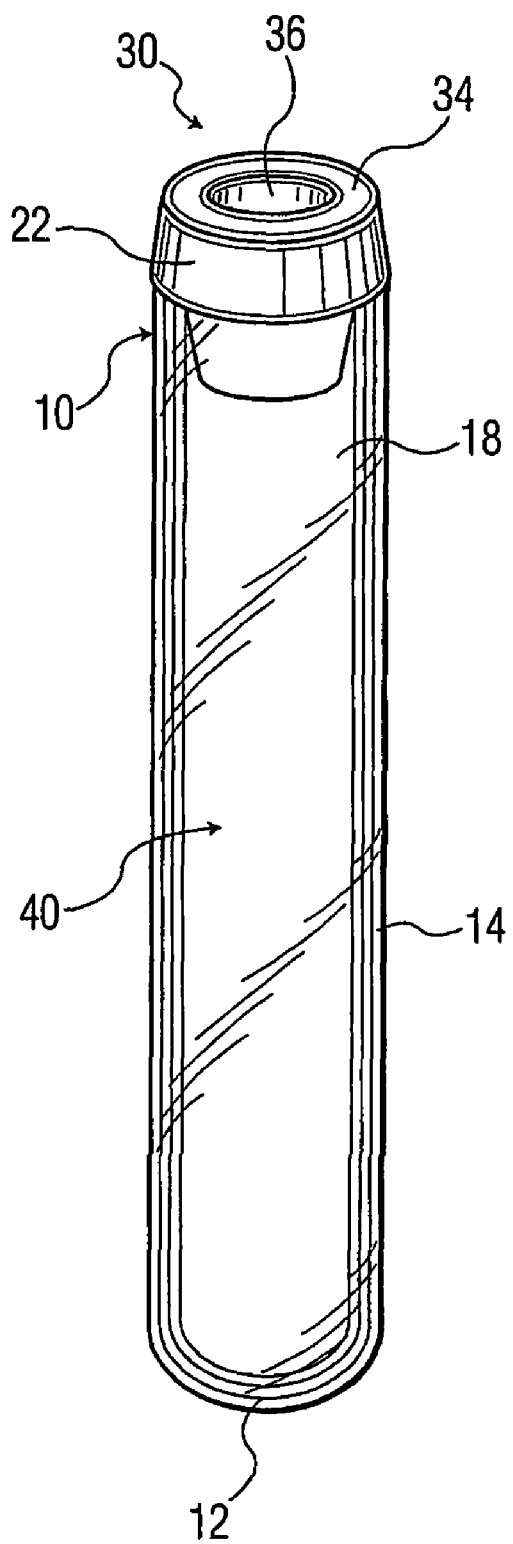
FIG. 4 is a perspective view of the blood collection assembly of the invention including the tube and closure of FIGS. 1-3.

FIGS. 1-4 illustrate a blood collection tube and closure according to an embodiment of the invention. In FIG. 1, tube 10 has bottom wall portion 12 and sidewall portion 14 continuous therewith. (The multilayer aspect of sidewall portion 14 is not shown in FIG. 1.) Sidewall portion 14 has a top edge 16 and defines an open end 18. A straight sidewall portion is shown for the tube 10, but complex sidewall shapes, for other containers, are also possible. FIGS. 2-3 illustrate a useful closure 20 for open end 18 of FIG. 1. Various other configurations for the closure, of any suitable materials, are possible. Closure 20 includes an annular upper portion 22 having a top wall 24. Upper portion 22 has a lower wall or lip 26, which extends over top edge 16 of tube 10 when the closure is in the tube. Stopper 20 also includes a lower annular portion or skirt 28 having an outside wall 30 which forms an interference fit with the inside wall surface of tube 10 to maintain the stopper in the tube. Skirt 28 also has an inside wall surface 32, which defines a well 34. Top wall 24 defines a cavity 36. A septum 38 separates well 34 and cavity 36 for penetration by a cannula when the tube assembly is ready for use. FIG. 4 illustrates the tube and stopper assembly ready for drawing a blood sample into enclosed interior space 40.

Figure 5:
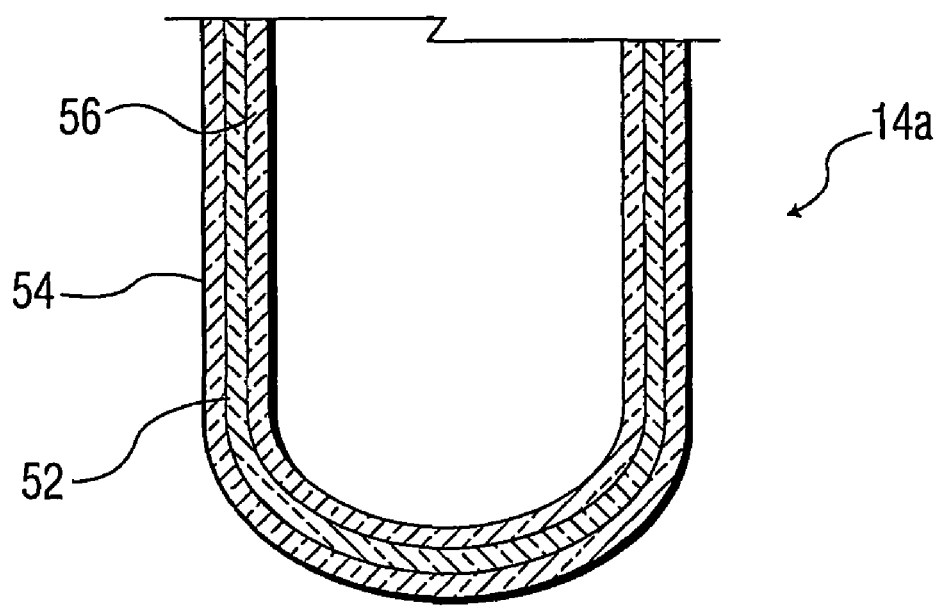
FIG. 5 is a horizontal sectional view of the tube of FIG. 1 taken along line 5-5 thereof.
Figure 6:
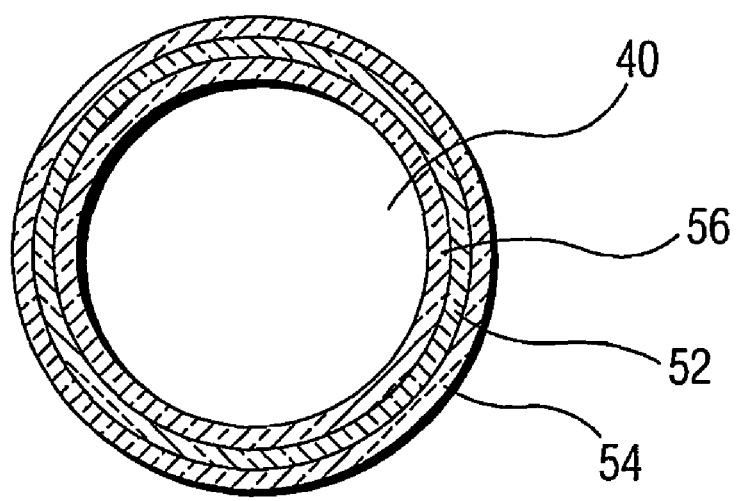
FIG. 6 illustrates a section of the wall of the tube of FIG. 1 along line 6-6.

The wall of the plastic tube 10 of the invention has multiple polymeric layers, generally discrete layers with no mixed interfacial regions. Configurations having three layers in a skin-core-skin arrangement, wherein the core layer is surrounded by inner and outer skin layers, are particularly useful. For example, FIGS. 5 and 6 show tube wall 14a having a core layer 52 surrounded by outer skin layer 54 and inner skin layer 56. Generally, the skin layers are of one material, with the core layer of another material.

The individual layers of the multilayer container of the invention are selected based on the contemplated use of the container. For blood collection tubes, as noted above, a combination of materials that inhibit gas and liquid vapor permeability are useful. Materials suitable for barrier materials include virgin polymers and copolymers having various linear or multi-branched molecular architectures or tacticites, including polyolefins and copolymers thereof (e.g., polyethylenes such as HDPE, LDPE, and LLDPE, polypropylene (PP), and cyclic olefin copolymers (COC)), polyvinylalcohol, ethylene vinyl alcohol copolymers (EVOH), polyvinyl chloride, polyvinylidene chloride, polyvinyl fluoride, polyvinylidene fluoride, polyamides, polyesters and copolyesters (e.g., polyethylene terephthalate or polyethylene naphthalate), polystyrene, polyacrylonitrile, polyacrylonitrile-butadiene-styrene, polystyrene-acrylonitrile copolymers, polycarbonate, polysulfones, liquid crystal polymers, polyacetals. Specific gas barrier materials include ethylene vinyl alcohol copolymer, polyester, or copolymers thereof, and specific liquid vapor barrier materials include cyclic olefin copolymers and polypropylene. Blends of materials are also possible, and as used herein, polymeric materials is intended to encompass such blends.

Organic or inorganic fillers, dyes, plasticizers, slip agents, processing aids, stabilizers and other small molecule additives may be added to impart improved properties to the base polymers, and, as used herein, the term polymeric material is intended to include polymers containing such additives. Other materials that may be of use include ultraviolet (UV) light barriers, molecular scavenger materials, radiation barrier materials, chargeable dyes (e.g., temperature sensitive), materials that react to temperature and/or pressure changes, and structural additives. It is also possible to use nanocomposites of the base polymers described above. Nanocomposites containing small amounts of clay (1-5%) have been shown to yield large improvements in barrier properties. A clay commonly used in these nanocomposites is organically modified montmorillonite, a mica-type silicate, which consists of sheets arranged in a layered structure. Nanoclays are used due to their high cation exchange capacity, high surface area, approximately 750 $m^2/g$ and large aspect ratio (larger than 50) with a platelet thickness of 100 nm. The large aspect ratio of the silicate layers force gas and liquid vapor molecules to follow a more tortuous path in the polymer matrix around the silicate layers promoting much larger diffusion distances, thereby lowering permeability. Orientation effects of the polymer matrix itself, also appears to lower the permeability of gas and liquid vapor molecules through the matrix.

Numerous combinations of materials are possible, disposed in any multilayer configuration, in the containers of the invention.

Generally, materials useful as gas barriers have the ability to provide a barrier to mass transfer of elements that are gases at typical atmospheric conditions, such as oxygen, carbon dioxide or nitrogen under a variety of environmental conditions such as temperature and humidity. The resistance to the mass transfer of gas at a certain partial pressure and temperature across a material of certain thickness and contact area can be expressed as the gas transmission rate with the units of [$cm^3$ mil/100 $in^2 \cdot 24$ hr•atm]. The suitability of a material as a good gas barrier material is determined by the application. Typically, a gas barrier to the transmission of air, which is approximately 79% Nitrogen and 21% oxygen, would have gas transmission rates less than 1.0 [$cm^3$ mil/100 $in^2 \cdot 24$ hr•atm] (23° C. 0% RH) for nitrogen and less than 15 [$cm^3$ mil/100 $in^2 \cdot 24$ hr•atm] (23° C. 0% RH) for oxygen.

Materials useful as liquid vapor barriers have the ability to provide a barrier to mass transfer of the gaseous vapors that exist above the surface of chemicals that are typically liquids at atmospheric conditions, the most common being water vapor. The pressure of these vapors is dependent upon temperature. The resistance to the mass transfer of liquid vapors at a certain partial pressure and temperature across a material of certain thickness and contact area can be expressed as the vapor transmission rate with the units of [g mil/100 $in^2 \cdot 24$ hr]. The suitability of a material as a good liquid vapor barrier material is determined by the application. Typically a good barrier to the transmission of water will have a liquid vapor transmission rates less than 1.0 [g mil/100 $in^2 \cdot 24$ hr] (@40° C. 90% RH). In addition, the material layer that will contact the blood (i.e., the internal skin layer) generally must be an acceptable clinical material, meaning that its interaction with the cellular and chemical components of drawn blood is acceptable for the end use of the sample.

COC and PP are readily available in the industry. Representative COC trade names are TOPAS (Hoechst Advanced Technology Group, Summit, N.J.), APEL (Mitsui Petrochemicals Industries) and Zeonex (Nippon Zeno Co.). A particularly useful COC is ethylene-dicyclopentadine copolymer.

Suitable EVOH polymers include those with 27-48% vinyl alcohol, which are commercially available. Suitable polyesters include PET and polyethylene naphthalate (PEN).

By way of example, It is possible to have a core layer of COC or PP (providing a liquid vapor barrier) and a skin layer of EVOH or polyester (to provide a gas barrier). It is also possible for the COC or PP to be the skin layer, with the core layer being EVOH or polyester. A particularly useful combination is PP and EVOH, in either configuration, although a configuration in which EVOH is the core material is particularly desirable for blood collection tubes. The proportion of skin thickness to core thickness is any suitable value that provides the desired properties.

An important feature of the multilayer container of the invention, particularly for evacuated blood collection tubes, is the coverage of each material. (Coverage, as used herein, indicates that a material is found in a cross-section of the container.) For example, if a liquid vapor barrier material is absent from a portion of the container, liquid vapor may escape. Thus, for some applications, it is important to have substantially continuous coverage of both a liquid vapor barrier material and a gas barrier material throughout both the bottom wall and throughout the side wall (throughout the side wall means up to within 0.1 inches of the top edge, but desirably the coverage is within 0.02 inches of the top edge).

Alternatively, it is possible to instead provide substantially continuous coverage of both materials up the sidewall only to a region of the container that will be contacted (e.g., sealed) by a stopper, since the presence of the stopper may provide sufficient barrier properties. (Substantially continuous coverage indicates that a material is found in at least 98% of the cross-section of the defined areas.) The formation process can be performed to provide the desired coverage. This is discussed in more detail below.

Depending on the materials used, it may also be important to encapsulate the core material, such that the amount of core material exposed to the outside environment is kept low. For example, if a particular property of a core material is affected by moisture present in the air, the formation process should be controlled such that the skin material substantially encapsulates the core material, thereby reducing or preventing exposure of the core material to the outside environment. In addition, encapsulation is useful where non-compatible polymers are used. (Non-compatible indicates polymers lacking good adhesion on a macroscale, meaning that upon formation of a two-layer film of two polymers, such polymers are considered non-compatible if they tend to delaminate immediately after the film-forming process or they tend to delaminate upon subsequent application of forces induced by normal handling, bending, object usage, changing environmental conditions (e.g., temperature change), or similar external factors.) Specifically, if two non-compatible materials were laminated together in a sheet, or even put into a two-layer tube configuration, e.g., by conventional 2-shot molding, it is likely that delamination would occur. But, in a skin-core-skin configuration according to the invention, delamination of non-compatible materials can be inhibited by encapsulating the core within the skin. The skin then physically restrains the core from delamination. For example, in a skin-core-skin embodiment where encapsulation and substantially continuous coverage are desired, the core material is present in all but the top edge of the container, and this top edge would instead have a cross-section of only the skin material. This edge would then restrain forces that might lead to delamination of the core material.

Containers of the invention are generally fabricated by coinjection molding, which is a process by which at least two separate injection moldable materials are combined just prior to the mold gate in an orderly one step molding operation, in which the materials co-flow for at least a portion of the operation. See, e.g., U.S. Pat. No. 5,914,138, the disclosure of which is hereby incorporated by reference. In particular, coinjection molding makes it possible to form an entire tube, including a closed, rounded bottom, in a single step, with desired coverage and desired encapsulation. No preform is needed. The bottom wall can be provided by using a mold cavity having a region for forming the closed bottom wall in a manner integral with the steps of flowing the polymer into the mold cavity. Desired coverage and/or encapsulation is achieved by controlling the flow of the various materials.

Figure 7:
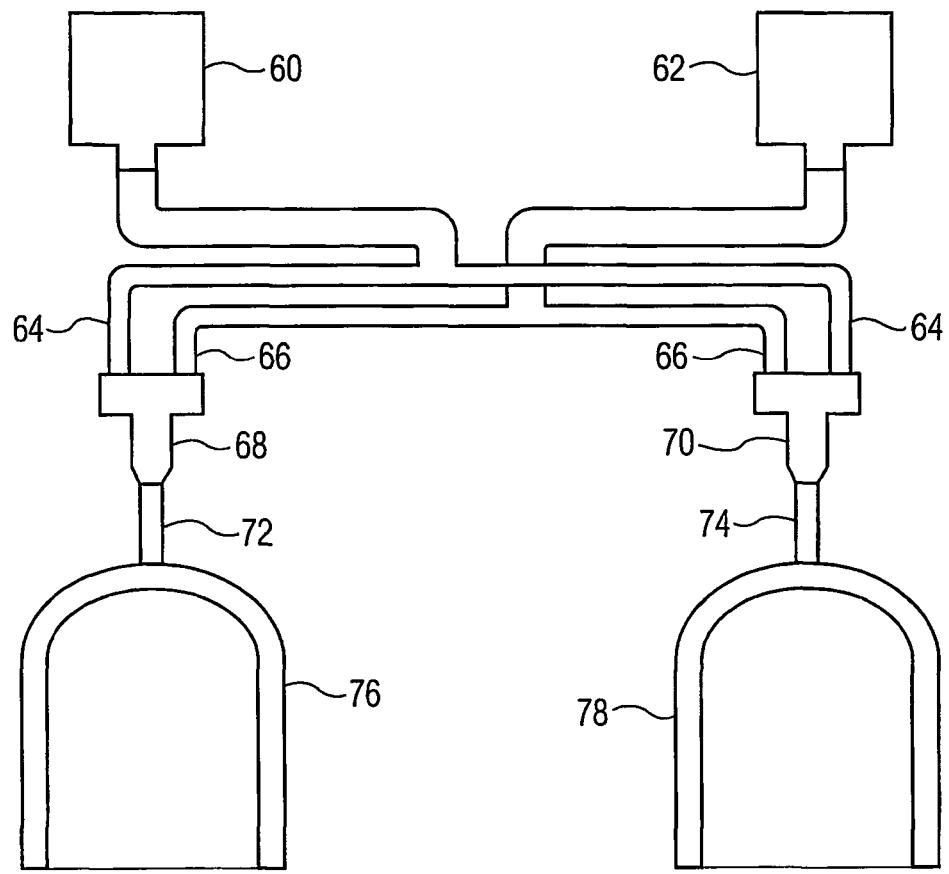
FIG. 7 shows a schematic of a co-injection configuration suitable for forming containers according to the invention.
Figure 8:
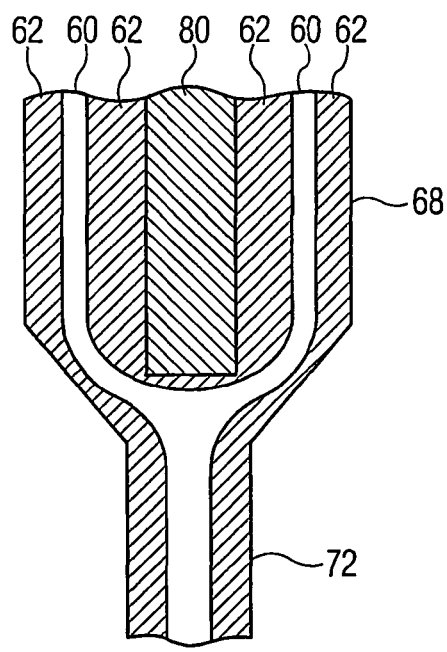
FIG. 8 shows a portion of a the co-injection configuration of FIG. 7.

To form 3-layer tubes according to the invention, a useful coinjection configuration and process is as follows, as reflected schematically in FIG. 7. (Generally, numerous mold cavities will be provided for each coinjection configuration, but only two mold cavities are shown in FIG. 7, for illustrative purposes.) The coinjection mold is a hot runner, valve gated, three-plate mold with a separate cold sprue 72, 74 for each cavity. Polymer melts of the core 60 and skin 62 materials are provided, e.g., by injection unit screw extruders. There are two separate manifolds 64, 66 which keep each polymer separate until reaching the nozzle section 68, 70 of the hot runner system. Maintaining this separation allows the two materials to be kept at different melt temperatures. At the nozzle 68, 70, three flow-fronts come together—an inner and an outer layer of skin material and an inner layer of core material. As the materials flow into the mold, the core material flows within the two skin layers. A valve-gate is used to positively shut-off material in the nozzle between shots. The nozzle 68, 70 feeds a cold sprue 72, 74 and then the tube regions 76, 78. Flow from the nozzle 68 is illustrated by FIG. 8. Core polymer 60 and skin polymer 62 flow together through the nozzle into the cold sprue 72, as three lamellar flows. Valve pin 80 is part of the overall valve gate that stops the flow of the polymer.

Figure 9:
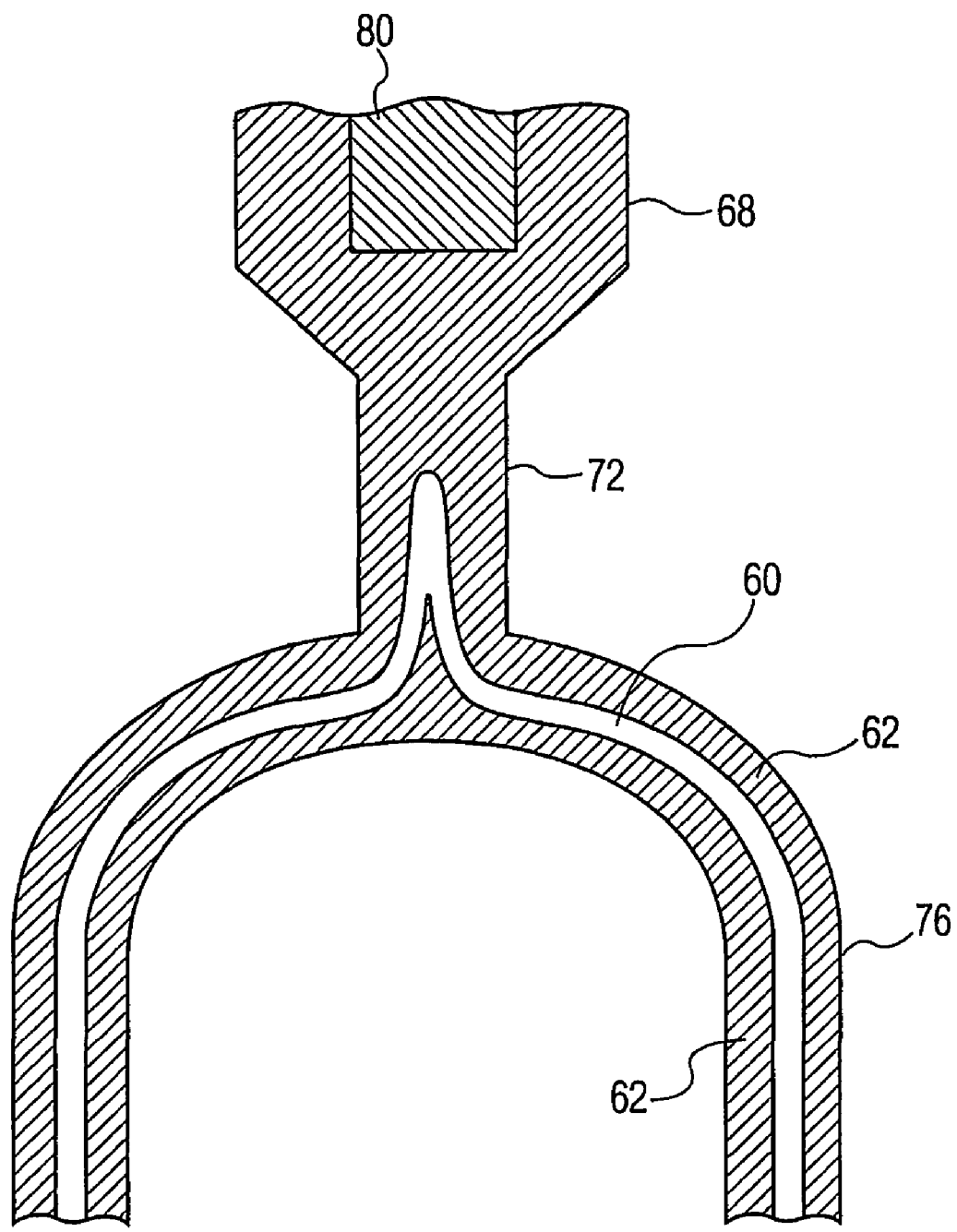
FIG. 9 shows another portion of the co-injection configuration of FIG. 7

As discussed above, it is possible for the coinjection process to provide substantially continuous coverage of the core material. For example, as reflected in FIG. 9, when a cold sprue 72 (also referred to as a sub-gate) is used, and some core material 60 is allowed to remain in the sprue at the end of a run, this extension of the core material provides the desired coverage in the bottom wall of the container. Allowing the core material into the cold sprue also lets a small amount of skin material clean out any remaining core material from the nozzle. This cleaning ensures that the following shot will start with skin material only and not be contaminated with core material. The three-plate mold is used to automatically degate the sprue from the tube and allow the sprues to be segregated from the tubes. Without this cold sprue, i.e., if the nozzle tip led directly into the tube region, a window would be created where the core layer injection was completed and only the skin layer material was being injected. This would create a significant region of the tube bottom that contained only skin material. Because the overall barrier properties of a multilayer component generally require coverage of both the core and skin materials, such a region is detrimental to the overall properties of the container. Thus, use of the cold sprue in the process of the invention provides advantages. In particular, as reflected in FIG. 10, when the cold sprue is removed from the mold, e.g., by shearing in the 3-plate mold, only a relatively tiny region at the tube bottom had no core material—the region is generally small enough to be insignificant, and the process is able to provide the substantially continuous coverage discussed above.

Another advantage to use of the cold sprue is the ability to use core materials that react poorly to environmental exposure. For example, EVOH is a useful gas barrier material, yet its oxygen barrier properties are detrimentally (but reversibly) affected if water vapor, e.g., from ambient air, is present in the EVOH. Therefore, while it may be possible to obtain good coverage of EVOH core material by co-flowing skin material and EVOH together through an entire cycle, such a process would cause EVOH to be exposed at the top edge of a tube as well as at the last-filled region of the tube. This exposure creates the potential for reduction of the tubes overall barrier properties. An additional feature of the invention is that no forming step subsequent to coinjection molding is generally required, e.g., a useful container is formed without a subsequent blow molding step.

The injection phase of co-injection molding is similar to monolayer molding. A typical process includes these steps:
  Close mold and build clamp pressure.
  Open cavity valve gate.
  Start skin material injection.
  Start core material injection when skin screw position reaches a predetermined set point (generally, the core and skin materials are simultaneously injected for at least 85% of the injection operation).
  Use velocity control to maintain the desired volumetric flow ratio of core flow rate to skin flow rate.
  Core injection transition.
  Core hold time and hold pressure.

Decompress core.
Close cavity valve gate at end of skin hold.
Cool.
Open mold, separate sprue from tube, open plates to eject sprue with air, and eject tube from core using stripper ring.

To control the proportion of skin layer thickness to core layer thickness, the volumetric flow rates of the skin and core material are adjusted. If the core is too thin relative to the wall thickness increasing the core injection velocity and feed stroke will increase the thickness and maintain coverage. If the core is too thick then decreasing the core injection velocity and feed stroke will correct this. This proportion is selected based on the materials and the end use of the container.

The containers of the invention are capable of being formed in any desired size. For example, a tube according to the invention is capable of being formed as a conventional evacuated tube 50-150 mm in length and 10-20 mm internal diameter. In particular, standard evacuated tubes, which are 75-100 mm in length and have a 13 mm internal diameter, or standard microcollection tubes, which are 43.18 mm long and have a 6.17 mm internal diameter, are possible. Typical wall thicknesses of conventional blood collection tubes, e.g., about 25 to about 50 mil, more typically about 30 to about 40 mil, are possible in tubes according to the invention. In a three-layer tube of the invention, for example, it is possible to have a core layer about 0.1 to about 20 mils thick, typically about 1 to 3 mils thick, with each skin layer being about 8 to about 40 mils thick, typically about 10 to about 30 mils thick.

For use in the specimen collection field, the container of the invention generally must go through additional processing steps. For examples, additives useful in blood or urine analysis, e.g., procoagulants or anticoagulants, are often disposed into the tube. As known in the art, blood analysis is often performed on serum, and procoagulants are typically used to enhance the rate of clotting. Such procoagulants, include silica particles or enzyme clot activators such as elagic acid, fibrinogen and thrombin. If plasma is desired for analysis, an anticoagulant is generally used to inhibit coagulation, such that blood cells can be separated by centrifugation. Such anticoagulants include chelators such as oxalates, citrate, and EDTA, and enzymes such as heparin.

Additives are disposed in the containers in any suitable manner, liquid or solid, including dissolution in a solvent, or disposing in powdered, crystallized, or lyophilized form.

It is also possible to include separators in the container, e.g., density gradient separators in mechanical or non-mechanical form (e.g., thixotropic gels). Such separators provide for cell separation or plasma separation, for example. See, e.g., European Patent applications EP1006360, EP1006359, EP1005909, EP1014088, EP1106253, and EP0384331, and U.S. Pat. Nos. 4,140,631, 4,770,779, 4,946,601, 6,406,671, 6,280,400, and 6,225,123.

Assembly of a container for use in specimen collection, after molding, may include placement of a density gradient separator, disposing an additive, subjecting the container to an evacuated chamber with a pressure below atmospheric pressure, applying a seal such as an elastomeric stopper or pierceable membrane, and sterilizing the container by a process such as irradiation (e.g., with cobalt 60 radiation), ethylene oxide gas exposure, or electron-beam exposure. (Note that several of these steps may be performed in an order other than that presented above).

Example 1

A PET tube and two multilayer tubes were made by a coinjection process as described above. All tubes were 16×100 mm size.

Run 1: PET tube with skin layer and core layer both PET.
Run 2: PET-COC-PET tube with inner and outer skin layers of PET and core layer COC.
Run 3: PEN-COC-PEN tube with inner and outer skin layers of PEN and core layer of COC.

Twenty tubes from each run were filled with 1 ml of water, evacuated to 200 mm Hg, and stoppered. The tubes were weighed. Ten tubes from each run were placed into a storage chamber at 25° C. and 50% relative humidity, and ten tubes from each run were placed in a storage chamber at 40° C. and 50% relative humidity. Average weight loss (i.e., water loss) for each run after 56 days is shown in Table 1.

TABLE 1

| Tube | Average water loss (mg) @ 25° C. after 56 days | Average water loss (mg) @ 40° C. after 56 days |
| --- | --- | --- |
| 1 | 58.3 | 163.9 |
| 2 | 13.2 | 50.5 |
| 3 | 6.0 | not measured |

Example 2

Three layer tubes of PP skin material and EVOH core material were fabricated according to the process described above. The tubes were 13 mm×75 mm, 2.0 ml draw tubes. Thirteen runs were made, the runs having variation in (1) the amount (volume percent) of EVOH present, and (2) the nominal extent of coverage of the EVOH in the tube, as shown in Table 2 below.

TABLE 2

| Nominal EVOH Coverage in Tube ⇒ | No EVOH in tube | EVOH located 0.500 inches from top edge and below | EVOH located 0.200 inches from top edge and below | EVOH located 0.500 inches from bottom of tube and above | Substantially Complete Coverage of EVOH |
| --- | --- | --- | --- | --- | --- |
| Nominal 0 vol. % EVOH | Run #1 | — | — | — | — |
| Nominal 5 vol. % EVOH | — | Run #5 | Run #4 | Run #3 | Run #2 |
| Nominal 8 vol. % EVOH | — | Run #9 | Run #8 | Run #7 | Run #6 |
| Nominal 10 vol. % EVOH | — | Run #13 | Run #12 | Run #11 | Run #10 |

For each run, multiple wet and dry tubes were prepared, and tested. Wet tubes were prepared by first weighing the empty tube, placing 0.2 ml of water therein, and reweighing.

The wet tubes were then conventionally evacuated and stoppered to provide a draw volume of 2.0 ml. Dry tubes were conventionally evacuated and stoppered to provide a draw volume of 2.0 ml. Draw volume at time 0 was determined as a control value for wet and dry tubes from each run.

The remaining tubes were placed in shelf packs and put into a chamber at 50° C., with no relative humidity control. Every seventh day for six weeks, 32 wet and 32 dry tubes from each run were removed for testing.

Figure 10:
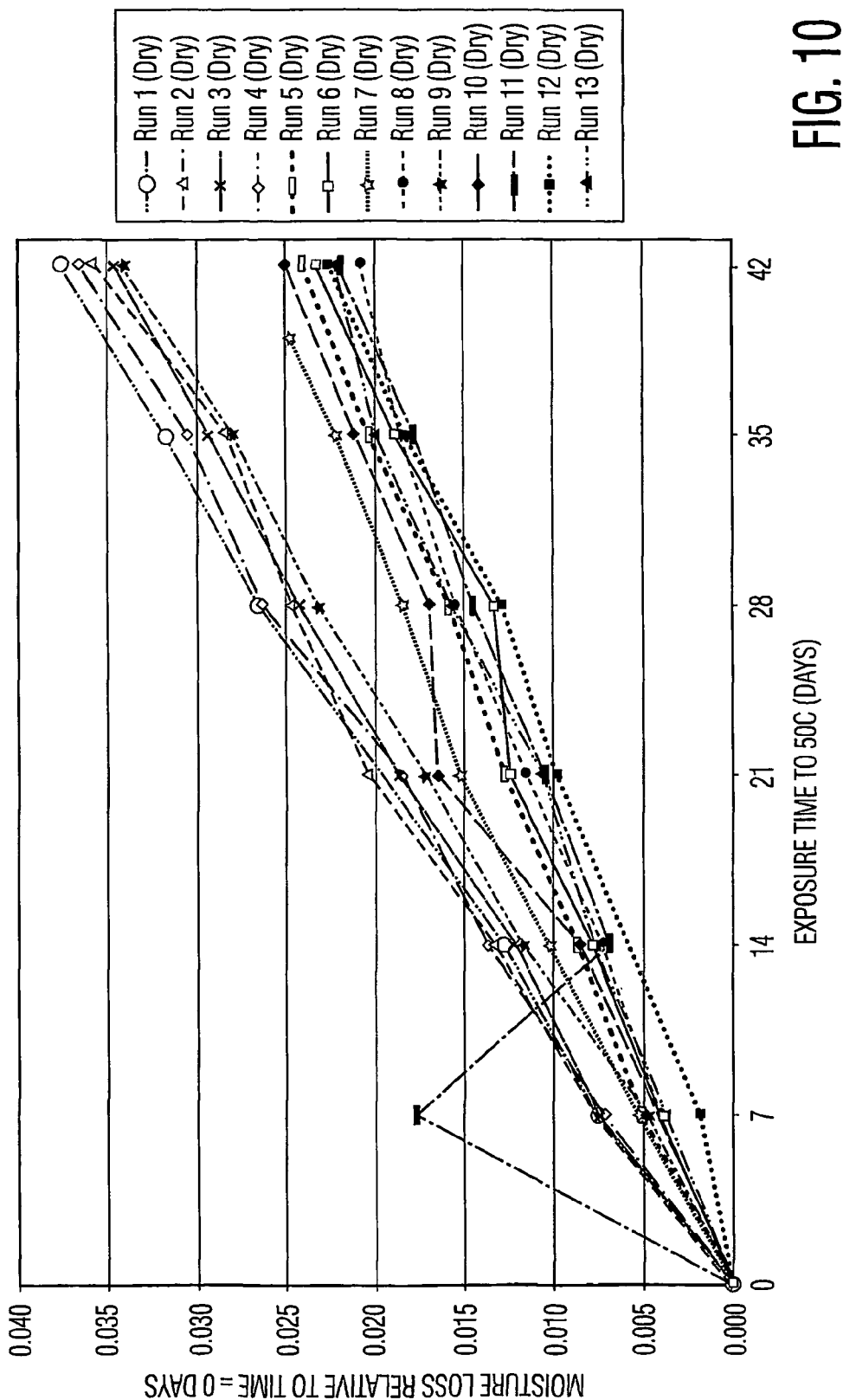
FIG. 10 shows moisture retention properties of tubes made according to the invention.
Figure 11:
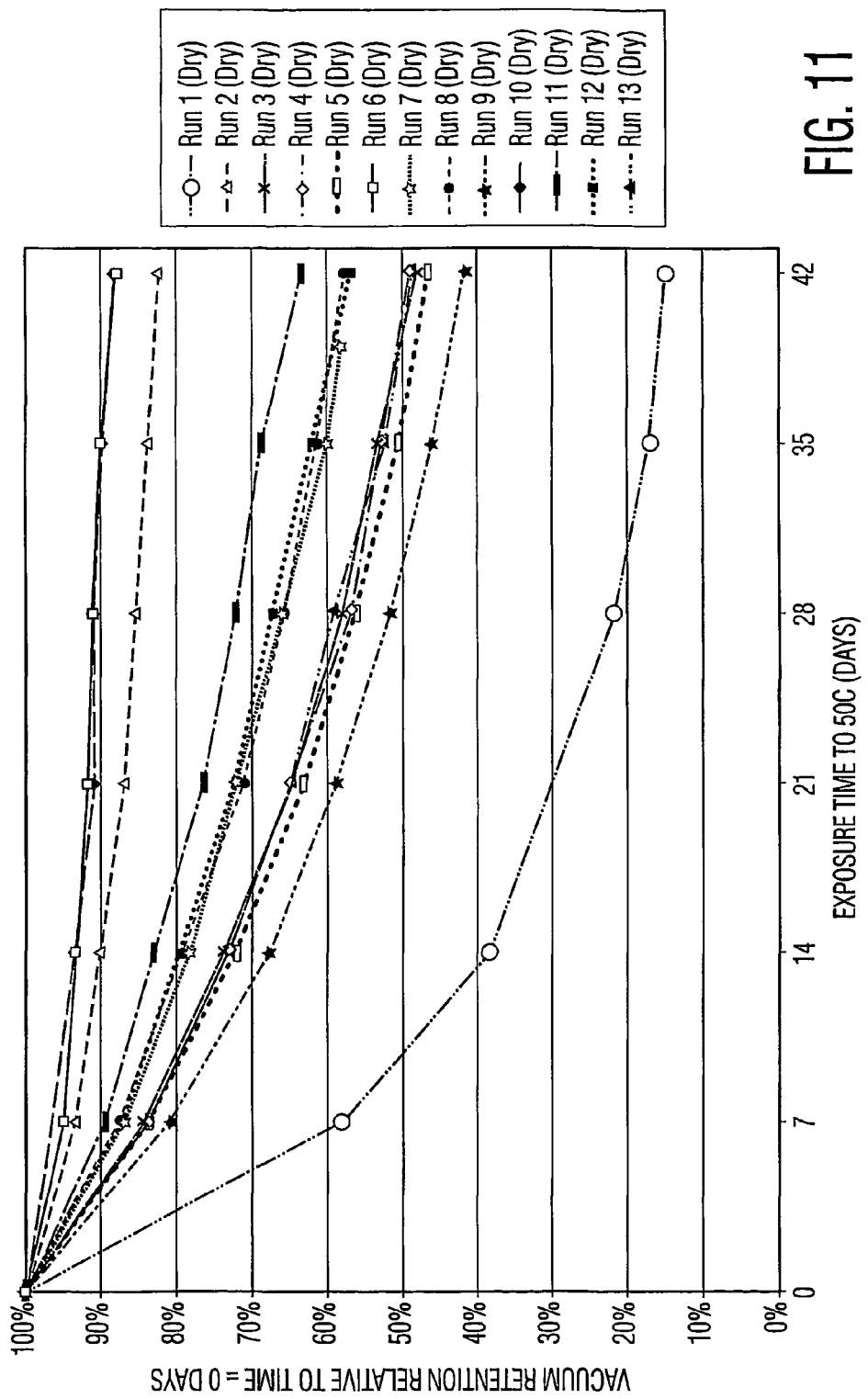
FIG. 11 shows vacuum retention properties of tubes made according to the invention.
Figure 12:
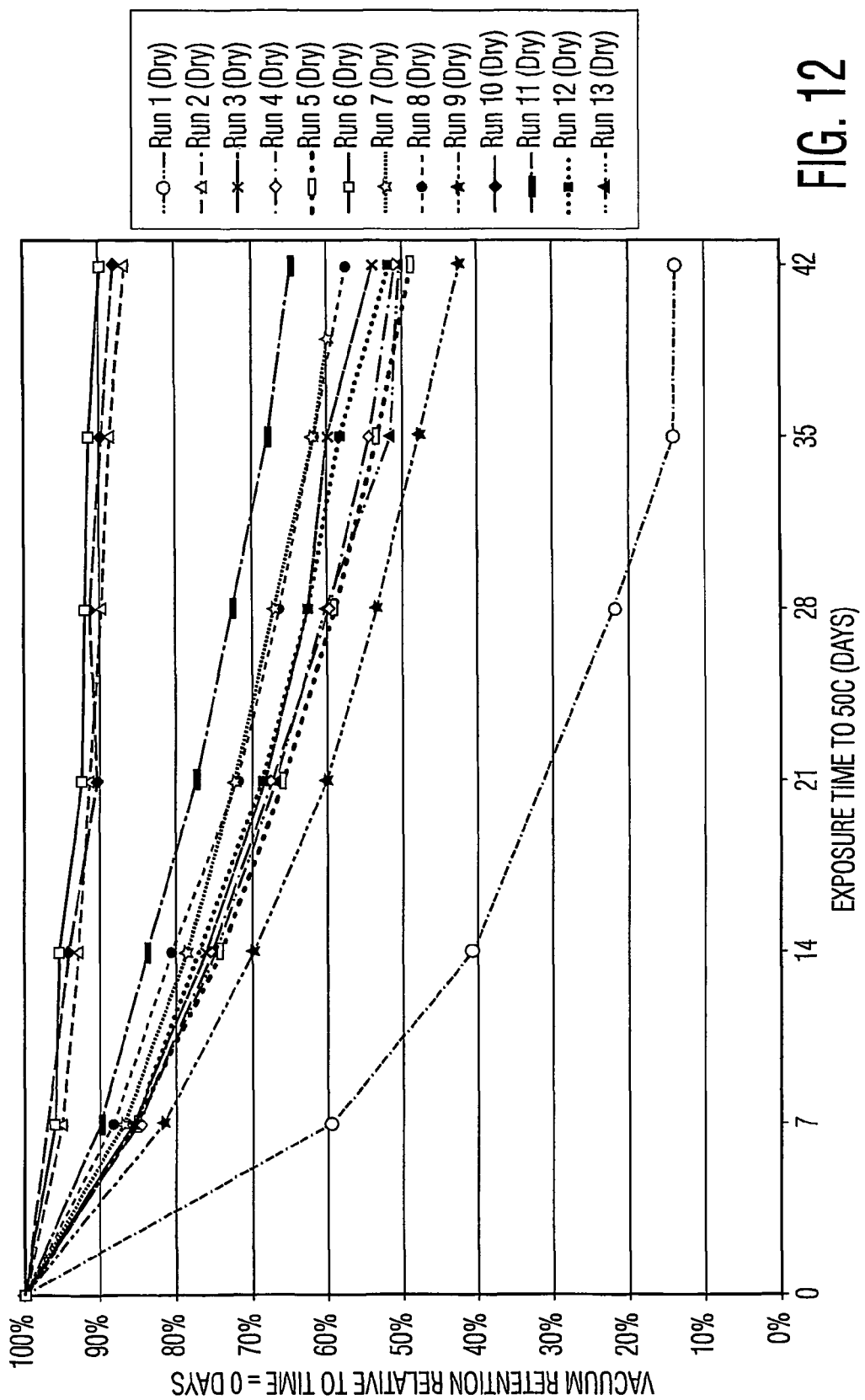
FIG. 12 shows vacuum retention properties of tubes made according to the invention.

For the wet tubes, testing was performed by weighing the tube to determine moisture loss, and then measuring draw volume to determine vacuum retention. For the dry tubes, testing was performed by measuring draw volume to determine vacuum retention. FIG. 10 shows the moisture loss testing results, FIG. 11 shows the vacuum retention testing results for the wet tubes, and FIG. 12 shows the vacuum retention testing results for the dry tubes.

Other embodiments of the invention are also possible, as will be apparent to one skilled in the art.

What is claimed is:

1. A process for fabricating a container having a bottom wall, a top edge, and a sidewall between the bottom wall and top edge, comprising the steps of:
    providing a first molten polymeric material and a second molten polymeric material, the first and second polymeric materials being non-compatible; and
    directing the first and second molten polymeric materials through a nozzle section, a cold sprue and into a mold cavity that comprises a region for integrally forming the bottom wall of the container, wherein the first and second molten polymeric materials co-flow in the mold cavity for at least a portion of the fabrication process, wherein, during the co-flow, the nozzle section directs the first and second molten polymeric materials into the mold cavity as inner and outer skin layers of the first molten polymeric material with a core layer of the second molten polymeric material between the inner and outer skin layers,
    removing the solidified first and second polymeric materials from within the cold sprue.

2. The process of claim 1, wherein the inner and outer skin layers are directly adjacent the core layer.

3. The process of claim 1, wherein the first and second polymeric materials are selected from the group consisting of ethylene vinyl alcohol copolymer, polyester, copolymers of ethylene vinyl alcohol copolymer and polyester, cyclic olefin copolymers, and polypropylene.

4. The process of claim 3, wherein the first and second polymeric materials are, respectively, polypropylene and ethylene vinyl alcohol copolymer, or cyclic olefin copolymer and ethylene vinyl alcohol copolymer, or polypropylene and polyester, or cyclic olefin copolymer and polyester.

5. The process of claim 4, wherein the first and second polymeric materials are, respectively, polypropylene and ethylene vinyl alcohol copolymer.

6. The process of claim 1, wherein the first polymeric material is a gas barrier material and the second polymeric material is a liquid vapor barrier material, or the first polymeric material is a liquid vapor barrier material and the second polymeric material is a gas barrier material.

7. The process of claim 1, wherein the core layer is encapsulated by the skin layers.

8. The process of claim 1, wherein the core layer exhibits substantially continuous coverage throughout the bottom wall and throughout the side wall.

9. The process of claim 1, wherein the core layer exhibits substantially continuous coverage throughout the bottom wall and in the side wall up to a region of the container that is intended to be contacted by a stopper.

10. A process for fabricating a container having a bottom wall, a top edge, and a sidewall between the bottom wall and top edge, comprising the steps of:
    providing a first molten polymeric material and a second molten polymeric material; and
    directing the first and second molten polymeric materials through a nozzle section into a mold cavity that comprises a region for integrally forming the bottom wall of the container,
    wherein the first and second molten polymeric materials co-flow in the mold cavity for at least a portion of the fabrication process,
    wherein, during the co-flow, the nozzle section directs the first and second molten polymeric materials into the mold cavity as annular inner and outer skin layers of the first molten polymeric material with an annular core layer of the second molten polymeric material between the inner and outer skin layers, and
    wherein a cold sprue is located between the nozzle section and the mold cavity, such that the polymeric materials pass through the cold sprue before flowing into the mold cavity and the polymeric materials are removed from the cold sprue after the co-flow portion of the fabrication process.

11. A process for fabricating a container having a bottom wall, a top edge, and a sidewall between the bottom wall and top edge, comprising the steps of:
    providing a first molten polymeric material, a second molten polymeric material, and a third molten polymeric material, the first and second polymeric materials being non-compatible, and the second and third polymeric materials being non-compatible; and
    directing the first and second and third molten polymeric materials through a nozzle section, a cold sprue and into a mold cavity that comprises a region for integrally forming the bottom wall of the container, wherein the first and second and third molten polymeric materials co-flow in the mold cavity for at least a portion of the fabrication process,
    wherein, during the co-flow, the nozzle section directs the first and second and third molten polymeric materials into the mold cavity as, respectively, an inner skin layer, a core layer, and an outer skin layer, with the core layer located between the inner and outer skin layers
    degating the cold sprue from the container or the mold cavity.

12. The process of claim 11, wherein the inner and outer skin layers are directly adjacent the core layer.

13. The process of claim 11, wherein the first, second, and third molten polymeric materials are identical or different, and one or more of the polymeric materials comprise one or more additives selected from the group consisting of organic or inorganic fillers, dyes, plasticizers, slip agents, processing aids, stabilizers, ultraviolet light barriers, molecular scavenger materials, radiation barrier materials, chargeable dyes, materials that react to temperature or pressure changes, and structural additives.

14. The process of claim 11, wherein the first and second and third polymeric materials are identical or different, and are selected from the group consisting of ethylene vinyl alcohol copolymer, polyester, copolymers of ethylene vinyl alcohol copolymer and polyester, cyclic olefin copolymers, and polypropylene.

15. The process of claim 11, wherein the first and second and third polymeric materials include at least one gas barrier material and at least one liquid vapor barrier material.

16. The process of claim 11, wherein the core layer is encapsulated by the skin layers.

17. The process of claim 11, wherein one or more of the first, second, and third polymeric materials comprise a nano-composite material.

18. The process of claim 1, wherein a substantially continuous annular core layer is formed in the container.

19. The process of claim 1, wherein only the first molten polymeric material flows in the mold cavity for the initial portion of the fabrication process.

20. The process of claim 10, wherein only the first molten polymeric material flows in the mold cavity for the initial portion of the fabrication process.

* * * * *